United States Patent [19]
Ionkin et al.

[11] Patent Number: 5,986,127
[45] Date of Patent: Nov. 16, 1999

[54] AMINONITRILE PRODUCTION

[75] Inventors: Alex Sergey Ionkin, Newark; Stanislaw Bogdan Ziemecki, Wilmington; Mark Jay Harper, Lewes; Theodore Augur Koch, Wilmington, all of Del.

[73] Assignee: E. I. du Pont de Nemours and Company, Wilmington, Del.

[21] Appl. No.: 09/268,148

[22] Filed: Mar. 15, 1999

Related U.S. Application Data

[60] Provisional application No. 60/078,838, Mar. 20, 1998.

[51] Int. Cl.$^6$ .................................................. C07C 255/00
[52] U.S. Cl. .............................................. 558/459
[58] Field of Search .............................................. 558/459

[56] References Cited

U.S. PATENT DOCUMENTS

| | | |
|---|---|---|
| 2,208,598 | 7/1940 | Rigby . |
| 2,245,129 | 6/1941 | Greenewalt . |
| 2,257,814 | 1/1941 | Rigby . |
| 2,762,835 | 9/1956 | Swerdloff . |
| 3,322,815 | 5/1967 | Feldman et al. . |
| 4,248,799 | 2/1981 | Drake . |
| 4,389,348 | 6/1983 | Diamond et al. . |
| 4,568,736 | 2/1986 | Curatolo et al. . |
| 4,601,859 | 7/1986 | Galle et al. . |
| 5,151,543 | 9/1992 | Ziemecki . |
| 5,296,628 | 3/1994 | Sanchez . |
| 5,527,946 | 6/1996 | Flick et al. . |

FOREIGN PATENT DOCUMENTS

| | | |
|---|---|---|
| 681932 | 11/1966 | Belgium . |
| 836 938 | 4/1952 | Germany . |
| 848 654 | 9/1952 | Germany . |

OTHER PUBLICATIONS

Mares et al., Preparation and Characterization of a Novel Catalyst for the Hydrogenation of Dinitriles to Aminonitriles, *Journal of Catalysis,* 112, 145–156, Apr. 20, 1987; revised Nov. 3, 1987.

*Primary Examiner*—Johann Richter
*Assistant Examiner*—Joseph Murray

[57] ABSTRACT

A process for selectively hydrogenating a dinitrile to an aminonitrile is provided. The process comprises contacting a dinitrile with a hydrogen-containing fluid in the presence of a solvent comprising an alcohol or liquid ammonia, at least one metal catalyst, and a carbonyl group-containing additive such as, for example, organic amides, organic esters, salts of carboxylic acids or urea.

25 Claims, No Drawings

AMINONITRILE PRODUCTION

This Application claims benefit of provisional application 60/078,838, Mar. 20, 1998.

FIELD OF THE INVENTION

The invention relates to a selective hydrogenation process for producing aminonitriles.

BACKGROUND OF TE INVENTION

Aminonitriles are a class of important chemicals which have a variety of industrial applications. For example, aminonitriles can be used as monomers for producing high molecular weight polyamides. Specifically, 6-aminocapronitrile can be used to produce nylon 6.

Aminonitriles can be produced by catalytic hydrogenation of dinitriles. However, the yield of and selectivity to a desired aminonitrile using processes known to one skilled in the art are generally not as high as one skilled in the art desires. Additionally, the amount of the complete hydrogenation product, diamine, is generally higher than one skilled in the art would desire.

A convenient process resulting in a high yield of aminonitriles at low levels of dinitrile starting materials, fully hydrogenated products (diamines) and byproducts would be of great usefulness for commercial production of aminonitriles.

Therefore, there is an increasing need to develop a process that can selectively hydrogenate a dinitrile to aminonitrile.

SUMMARY OF THE INVENTION

It is the object of the present invention to provide a process for the product of aminonitriles from dinitriles. An advantage of this invention is that an aminonitrile can be produced in high yield and having a high selectivity to the aminonitrile. Other objects and advantages will become more apparent as the invention is more fully disclosed hereinbelow.

This invention provides a process for the selective or partial hydrogenation of a dinitrile to an aminonitrile. The process comprises contacting a dinitrile with a hydrogen-containing fluid in the presence of (a) a solvent comprising liquid ammonia, an alcohol, or both; (b) a hydrogenation catalyst; and (c) a carbonyl group-containing organic compound additive.

DETAILED DESCRIPTION OF THE INVENTION

According to this invention, a dinitrile having the formula of NCRCN is contacted with a hydrogen-containing fluid in the presence of a solvent, a catalyst, and a carbonyl group-containing organic compound additive selected from the group consisting of organic amides, organic esters and salts of carboxylic acids, in which R is a hydrocarbylene group selected from the group consisting of alkylene group, arylene group, alkenylene group, alkarylene group, aralkylene group, and combinations of two or more thereof. The presently preferred R is an alkylene group. Each hydrocarbylene group can contain about 2 to about 25, preferably about 2 to about 15, and most preferably 2 to 10 carbon atoms per group. In other words, a suitable dinitrile can contain about 4 to about 27, preferably about 4 to about 17, and most preferably about 4 to about 12 carbon atoms per dinitrile molecule.

Examples of suitable dinitriles include, but are not limited to, adiponitrile, methylglutaronitrile, alpha, omega-propanedinitrile, alpha, omega-butanedinitrile, alpha, omega-pentanedinitrile, alpha, omega-heptanedinitrile, alpha, omega-nonanedinitrile, alpha, omega-dodecanedinitrile, alpha, omega-pentadecanedinitrile, alpha, omega-icosanedinitrile, alpha, omega-tetracosanedinitrile, 3-methylhexanedinitrile, 2-methyl-4-methyleneoctanedkiitrile, and combinations of two or more thereof The presently preferred dinitrile is adiponitrile because its selective hydrogenation product, 6-aminocapronitrile, is a well-known monomer for polymerization applications.

Any hydrogen-containing fluid can be used in the invention as long as there is sufficient hydrogen in the fluid to selectively hydrogenate a dinitrile to an aminonitrile. The term "fluid" refers to liquid, gas, or both. The hydrogen content in the fluid can range from 1 to 100%, preferably about 50 to about 100%, and most preferably 90 to 100% by volume. The presently preferred hydrogen-containing fluid is a pure hydrogen gas.

The molar ratio of hydrogen (in the hydrogen-containing fluid) to dinitrile is not critical as long as sufficient hydrogen is present to produce the desired aminonitrile. Hydrogen is generally used in excess. Hydrogen pressures are generally in the range of about 50 to about 2000 psi (0.345 to 13.79 MPa), with about 200 to about 1000 psi (1.42 to 6.89 MPa) preferred.

Any solvent that comprises either liquid ammonia or an alcohol can be used in the invention. The concentration of liquid ammonia in the solvent can range from about 20 to about 100%, preferably about 50 to about 100%, and most preferably about 80% to about 100%, by weight of total solvent. A pure liquid ammonia is presently preferred. However, if an alcohol is also present in the solvent, the concentration of ammonia can be adjusted based on the quantity of alcohol used which is disclosed hereinbelow. The molar ratio of ammonia to dinitrile can generally be in the range of from about 1:1 to about 30:1, preferably about 2:1 to about 20:1.

Any alcohol that can facilitate the selected hydrogenation of a dinitrile to an aminonitrile can be used in this invention. The presently preferred alcohol has one to about 10, preferably one to about 4, carbon atoms per molecule. Examples of suitable alcohol include, but are not limited to, methanol, ethanol, propanol, isopropyl alcohol, butanol, isobutyl alcohol, pentanol, hexanol, heptanol, octanol, nonanol, decanol, and combinations of two or more thereof The presently most preferred alcohol is methanol. The alcohol can generally be present in the solvent in the concentration of from about 10 to about 100%, preferably about 30 to about 99%, by weight.

The alcohol solvent can further comprise a base which is substantially soluble in the solvent. The term "substantially" refers to "more than trivial". The presently preferred base is an inorganic base. Examples of inorganic bases include, but are not limited to, alkali metal oxides, alkaline earth metal oxides, alkali metal hydroxides, alkaline earth metal hydroxides, partially neutralized acids in which one or more protons of the acids are replaced with ammonium ion, alkali metal ions, alkaline earth metal ions, or combinations of two or more thereof Examples of suitable bases include, but are not limited to lithium hydroxide, sodium hydroxide, sodium oxide, potassium hydroxide, sodium bicarbonate, sodium carbonate, potassium bicarbonate, or combinations of two or more thereof The presently most preferred bases are ammonia, lithium hydroxide, and sodium hydroxide for they are readily available and inexpensive.

A base can be present in the solvent in any quantity so long as the quantity can facilitate the selective hydrogenation of a dinitrile to an amino nitrile. Generally, a base can be present in the solvent in the range of from about 1 to about 10 weight %, based on the total weight of the dinitrile.

The catalyst in the process is selected from the group consisting of iron, cobalt, nickel, rhodium and magnesia-supported nickel-iron. The catalyst may also contain one or more promoters, for example, chromium, molybdenum, and tungsten. The catalyst can also be in the form of an alloy such as, for example, Raney nickel, in the form of individual metal, or in the form of solid solution of two or more metals.

The catalytic metal can also be supported on an inorganic support such as alumina, magnesium oxide, and combinations thereof The metal can be supported on an inorganic support by any means known to one skilled in the art such as, for example, impregnation, coprecipitation, ion exchange, and combinations of two or more thereof. The presently preferred inorganic support is magnesium oxide.

Any additive that can effect the selectivity improvement can be used in the invention. The term "improvement" is referred to as enhanced selectivity to aminonitrile product at conversions greater than about 70%, preferably conversions greater than about 80%, as compared to the selectivity without the use of the additive of this invention. Presently, the preferred additive is a carbonyl group-containing organic compound additive selected from the group consisting of organic amides, organic esters and salts of carboxylic acids.

Examples of suitable carbonyl-containing organic compounds include, but are not limited to, formamide, acetamide, N-methyl formamide, N,N-dimethyl formamide, N-methylacetamide, N-methyldodecanamide, methyl formate, ethyl formate, sodium formate, ammonium formate and urea, and combinations of two or more thereof.

The additive can be present during the contacting in any quantity which can improve the selective hydrogenation of a dinitrile to its corresponding aminonitrile. Generally, the weight ratio of the additive to the catalyst can be in the range of from about 0.001:1 to about 0.5:1, preferably about 0.001:1 to about 0.1:1.

The catalyst metal can be present in any physical shapes or forms. It can be in fluidizable forms, extrudates, tablets, spheres, or combinations of two or more thereof. The catalyst may be in sponge metal form, for example the Raney nickels and Raney cobalts. The molar ratio of a catalyst to dinitrile can be any ratio as long as the ratio can catalyze the selective hydrogenation of a dinitrile. The weight ratio generally can be in the range of from about 0.0001:1 to about 1:1, preferably about 0.001:1 to about O.5:1. The process can be carried out in batch or continuous mode. If the catalytic metal is supported on an inorganic support or is a portion of alloy or solid solution, the catalytic metal can be present in the range of from about 0.1 to about 60, preferably about 1 to about 50, and most preferably about 2 to about 50 weight %, base on the total weight catalytic metal and inorganic support.

Catalyst and an additive disclosed above can be separately introduced into contact with a dinitrile. However, it is presently preferred that a catalyst, whether it is in its metal form or in an alloy or solid solution or on an inorganic support, preferably in a solvent is contacted with an additive disclosed above. The solvent can be an alcohol, an ether, an ester, ammonia or combinations of two or more thereof. Further preferably the contacting of a catalyst and an additive is also carried out in a hydrogen-containing fluid. The hydrogen-containing fluid can be the same as that disclosed above. Contacting of a catalyst and an additive produces a pretreated catalyst. The pretreated catalyst can be washed with a solvent disclosed above, preferably under anaerobic condition to produce an additive-treated catalyst.

The contacting of a catalyst and an additive can be carried out under any conditions effective to produce an additive-treated catalyst which can improve selective hydrogenation of a dinitrile or the selectivity to an aminonitrile. Generally, the entire process for producing the additive-treated catalyst can be carried out by contacting a catalyst with an additive disclosed above at a temperature in the range of from about 20° C. to about 150° C., preferably about 30° C. to about 100° C. under a pressure in the range of from about 0.5 to about 100 atmospheres (atm) for about 5 seconds to about 25 hours.

Preferably the carbon atoms of the starting dinitrile are arranged in a branched or linear chain. Preferred examples are the hydrogenation of adiponitrile to 6-aminocapronitrile, methylglutaronitrile to two isomeric aminonitriles (5-amino-2-methylvaleronitrile and 5-amino-4-methylvaleronitrile), and alpha, omega-dodecanedinitrile to the corresponding aminonitrile. A most preferred application of the process of the present invention is to maximize the formation of 6-aminocapronitrile to simplify the production nylon 6.

The process of the present invention can be carried out at a temperature in the range of from about 25 to 150° C., preferably 40 to 100 ° C., most preferably 60 to 80° C. at a total pressure from about 0.345 to about 13.8 MNa, preferably about 1.7 to about 6.9 MPa for about 15 minutes to about 25 hours, preferably about 1 hour to about 10 hours.

The presently preferred catalyst is a sponge metal type catalyst The metallic component is iron, cobalt or nickel. Commercially available catalysts of this type are promoted or unpromoted Raney Ni or Raney Co catalysts which can be obtained from the Grace Chemical Co. (Columbia, Md.), Activated Metals Corporation (Sevierville, Tenn.) or Degussa (Ridgefield Park, N.J.). The metal catalyst, as disclosed above, can be supported on an inorganic support such as, for example, iron/nickel on magnesium oxide composition can be used as catalyst. In the case of the use of the supported nickel iron catalyst, the rate of adiponitrile conversion increases with the amount of Ni deposited on the support. The preferred concentration of Ni is between 5 and 50% (wt % of nickel in the metal/support composition), and especially between 25 and 35%. The iron present in the nickel/iron/ magnesium oxide composition can be between 0.2% and 20% of the Ni/Fe/MgO composition, most preferably 0.5% to 10%.

Wishing not to be bound by theory, it is believed that addition of an additive to, or use of additive-treated, catalyst in the selective hydrogenation process results in modification of the catalyst thereby improving or enhancing the selectivity to aminonitrile, comparing to results obtained in the absence of such additives.

The process of the invention can be operated batch wise or continuously in an appropriate reactor. Stirring or agitation of the reaction mixture can be accomplished in a variety of ways known to those skilled in the art. The partial hydrogenation of the starting dinitrile to its corresponding aminonitrile with high selectivity at high conversions of the dinitrile makes this process efficient and useful.

The following examples further illustrate the process of the invention and are not to be construed to unduly limit the scope of the invention.

EXAMPLES

Definitions

The meaning of terms used in the Examples is defined as follows.

Yield of aminonitrile is the measured concentration of aminonitrile divided by the starting concentration of dinitrile.

Conversion of the dinitrile is the difference between the starting and the instant concentration of dinitrile, divided by the starting concentration of dinitrile.

Selectivity to aminonitrile is the measured yield of aminonitrile divided by conversion of the dinitrile at that instance.

Comparative Example 1

Raney Ni (1.2 g) promoted with Fe and Cr (Activated Metals, A4000, without any further additives) was added to a 50 cc autoclave together with 3.2 g adiponitrile (ADN) and 35cc of liquid ammonia to form a mixture. Hydrogen was introduced to the autoclave and the ADN was hydrogenated at 60° C. under the total pressure of 1045 psig (at about 1500 rpm). Total conversion of ADN was reached within 30 minutes on stream. The maximum yield of aminocapronitrile reached 57%, for selectivity of 71% at 80% ADN conversion, and 63% at 90% ADN conversion.

Comparative Example 2

To a 300 cc autoclave, was charged 7.7 g Raney Co (obtained from W.R race Co.), 0.77 g water, 26 g ADN, and 139 g liquid ammonia. The content was hydrogenated at 70° C., under the total pressure of 1000 psig, at 1000 rpm. Total conversion of ADN was reached within 40 minutes on stream. The maximum yield of aminopronitrile reached 58%, for selectivity of ca 74% at 80% ADN conversion, and ca 64% at 90% ADN conversion.

Example 1

A 50 cc autoclave was charged with 3.2 g ADN, 1.2 g Raney Mi, 1.5 g of formamide, and 34.5 cc of liquid ammonia. The mixture was heated to 80° C., then brought in contact with hydrogen for a total pressure of 1000 psig, and run for 3 hrs with efficient stirring. The maximum yield of aminocapronitrile reached ca. 76% after two hours on stream, then started to decrease, as the concentration of hexamethylenediamine in the reaction mixture began to grow. The selectivity to aminocapronitrile was ca 88% at 80% ADN conversion, and ca 85% at 90% conversion.

Example 2

Pretreatment of Catalyst with Formamide 3.6 g Raney Ni was charged into a 50 cc autoclave, together with 4.5 g of formamide. Subsequently 35 cc of liquid ammonia was added, and the mixture was heated to 80° C. with stirring; the pressure was adjusted to 1000 psig with hydrogen, then kept under such conditions for 2.5 hrs. After cooling the pressure, was released, the sample was transferred to a dry box, washed with deaerated methanol, and stored under anaerobic conditions.

Example 3

1.2 g of the Raney Ni, pretreated with formamide as described in Example 2 and kept in a dry box for 10 days, was charged into the autoclave together with 3.2 g ADN and 35 cc of liquid ammonia, heated to 70° C., and reacted with hydrogen at a total pressure of 1000 psig. No additional formamide was added to the reaction mixture. The selectivity to aminocapronitrile was ca 93% at 80% ADN conversion, and ca 86% at 90% conversion.

Example 4

1.2g of Raney Co, pretreated with formamide in a way analogous to that described in Example 2 for Raney Ni catalyst, was charged together with 3.2 g ADN and 35 cc of liquid ammonia, heated to 70° C., and hydrogenated at total pressure of 1000 psig. The selectivity to aminocapronitrile was ca 84% at 80% ADN conversion, and ca 79% at 90% conversion.

Example 5

To a 160 cc autoclave was charged 9.6 g AWN, 3.6 g Raney Co, and 4.5 g formamide. Then transferred 50 g of liquid ammonia, and hydrogenation at a total pressure of 1000 psig was carried out for 3.5 hours. The maximum yield of aminocapronitrile was 63%. The selectivity to aminocapronitrile was ca 78% at 80% ADN conversion, and ca 70% at 90% conversion.

Example 6

A 50 cc autoclave was charged with 1.2 g of Raney Ni, that had been pretreated with N-methylformamide similarly to the method used in Example 2, 3.2 g ADN, and 35 cc of liquid ammonia. No additional N-methylformamide was added to the reaction mixture. The reaction mixture was hydrogenated at 70° C. and 1000 psig total pressure. The maximum yield of aminocapronitrie was ca. 73%. The selectivity to aminocapronitrile was ca. 88% at 80% ADN conversion, and ca 81% at 90% conversion.

Example 7

Hydrogenation reaction as described in the Example 6 was carried out at 80° C. The maximum yield of aminocapronitrile was ca. 73%. The selectivity to aminocapronitrile was ca. 86% at 80% ADN conversion, and ca 81% at 90% conversion.

Example 8

A 50 cc autoclave was charged with 1.2 g of Raney Ni, that had been pretreated with ammonium formate similarly to the method used in Example 2, 3.2 g ADN, and 35 cc of liquid ammonia. No additional ammonium formate was added to the reaction mixture. The reaction mixture was hydrogenated at 80° C. and 1000 psig total pressure. The maximum yield of aminocapronitrile was ca. 68%. The selectivity to aminocapronitrile was ca. 81% at 80% ADN conversion, and ca 76% at 90% conversion.

Example 9

A 50 cc autoclave was charged with 3.2 g ADN, 1.2 g Raney Ni pretreated with acetamide, in a manner similar to that of Example 2, and 35 cc of liquid ammonia. The mixture was heated to 60° C., then brought in contact with hydrogen for a total pressure of 1000 psig, and run for 1 hour with efficient stirring. The maximum yield of aminocapronitrile reached ca. 65%. The selectivity to aminocapronitrile was about 79% at 80% ADN conversion, and about 73% at 90% conversion.

Example 10

A 50 cc autoclave was charged with 1.2 g of Raney Ni catalyst previously pretreated with ethyl formate, 3.2 g adiponitrile, and 35 cc of liquid ammonia The mixture was hydrogenated at 80° C. and 1000 psig total pressure. The maximum yield of 6-aminocapronitrile was ca. 75%, for 6-aminonitrile selectivity of ca. 88% at 80% adiponitrile conversion, and ca. 83% at 90% conversion.

Example 11

A sponge metal Fe promoted with Co and Ni was prepared, by leaching, from the alloy containing initially 60% Al, 30% Fe, 9 % Co, and 1% Ni by weight. This catalyst was pretreated with formamide as described in Example 2. A 50 cc autoclave was charged with 1.2 g of the formamide-pretreated sponge metal Fe, 3.2 g adiponitrile containing the internal standard, and 35 nm of liquid ammonia. The system was pressurized with hydrogen to total pressure of 1000 psig, and the reaction was carried out at 70° C. at that pressure. The maximum yield of aminocapronitrile was 66% at ca 85% ADN conversion, thus selectivity ca. 77%. Total conversion of ADN was reached after approximately 2.5 hours on stream.

Example 12

A sponge catalyst Ni-Co promoted with Cr was prepared, by leaching, from the alloy containing initially 54% Al, 23% Ni, 23% Co, and 1% Cr by weight. This catalyst was pretreated with formamide as described in Example 2. A 50 cc autoclave was charged with 1.2 g of the formamide-pretreated sponge metal Ni, 3.2 g adiponitrile containing the internal standard, and 35 mL of liquid ammonia. The system was pressurized with hydrogen to total pressure of 1000 psig, and the reaction was carried out at 80° C. at that pressure. The maximum yield of aminocapronitrile was 74% at ca. 87% ADN conversion, thus selectivity ca. 85%. Total conversion of ADN was reached after approximetely 4.5 hrs on stream.

Comparative Example 3

The catalyst described in the Example 13, but not pretreated, was tested in the ADN hydrogenation reaction in $NH_4OH$ solvent. A 100 mL autoclave was charged with 1 g of the activated catalyst, 10 g of ADN mixed with 5 g MeOH and containing the internal standard, and 26.2 g of the 30% OHNLOI-L pressurized with hydrogen to 500 psig, and run at 75° C. The maximum yield of aminocapronitrile was 58% at 76% ADN conversion, thus selectivity of 76%.

Example 13

A 50 cc autoclave was charged with 3.2 g ADN, 1.2 g Raney Ni pretreated with urea in a manner similar to that of Example 2, and 35 cc of liquid ammonia. The mixture was heated to 60° C., then brought in contact with hydrogen at a total pressure of 1000 psig, and reacted with efficient stirring at that temperature. After 1 hr on stream the yield of aminocapronitrile was 72%, at 85% of adiponitrile conversion, for the selectivity to aminocapronitrile of 84%.

Example 14

A 50 cc autoclave was charged with 9.6 g ADN, 1.2 g Raney Co pretreated with ethyl formate in a manner similar to that of Example 2, and 16 cc of liquid ammonia. The mixture was heated to 80° C., then brought in contact with hydrogen at a total pressure of 1000 psig, and reacted with efficient stirring at that temperature. After 2.5 hrs on stream the yield of aminocapronitrile was 67%, at 77% of adiponitrile conversion, for the selectivity to aminocapronitrile of 87%.

Pertinent results of the above runs are summarized in the following table.

| Example | Catalyst | Additive | Time, hour | Sel., % | Conv., % |
|---|---|---|---|---|---|
| comp. 1 | Raney Ni | none | 0.5 | 71 | 80 |
| comp. 2 | Raney Co | none | 0.7 | 74 | 80 |
| 1 | Raney Ni | formamide | 2 | 88 | 80 |
| 3 | Raney Ni[a] | formamide | 1.7 | 93 | 80 |
| 4 | Raney Co[a] | formamide | 3.5 | 84 | 80 |
| 5 | Raney Co | formamide | 0.7 | 78 | 80 |
| 6 | Raney Ni | N-meth. formamide[e] | 1.7 | 88 | 80 |
| 7 | Raney Ni[b] | N-meth. formamide[e] | 0.7 | 86 | 80 |
| 8 | Raney Ni[b] | amm. formate[f] | 2 | 81 | 80 |
| 9 | Raney Ni[a] | acetamide | 3.5 | 79 | 80 |
| 10 | Raney Ni[a,b] | ethyl formate | 0.7 | 88 | 80 |
| 11 | Raney Fe/CoNi[a] | formamide | 1.7 | 77 | 85 |
| 12 | Raney NiCo/Cr[a] | formamide | 2.8 | 76 | 87 |
| comp. 3 | Raney NiCo/Cr[c] | none | 1.5 | 76 | 76 |
| 13 | Raney Ni[a,d] | urea | 1 | 84 | 85 |
| 14 | Raney Co[a,b] | ethyl formate | 2.5 | 87 | 77 |

Footnote:
All hydrogenation experiments run at 1000 psig total, at 70° C. unless otherwise indicated.
[a] catalyst pretreated with an additive;
[b] run at 80° C.;
[c] at 75° C.;
[d] at 60° C.;
[e] N-methyl formamide; and
[f] ammonia formate.

What is claimed is:

1. A process for producing an aminonitrile comprising contacting a dinitrile with a hydrogen-containing fluid in the presence of a solvent comprising liquid ammonia or an alcohol, at least one metal catalyst, and an additive comprising a carbonyl group-containing organic compound.

2. The process according to claim 1 wherein said dinitrile is an aliphatic dinitrile.

3. The process according to claim 2 wherein said dinitrile has about 4 to about 12 carbon atoms per molecule.

4. The process according to claim 1 wherein the molar ratio of said ammonia to said dinitrile is in the range of from about 1:1 to about 30:1.

5. The process according to claim 1 wherein the molar ratio of said ammonia to said dinitrile is in the range of from about 2:1 to about 20:1.

6. The process according to claim 3 wherein the molar ratio of said ammonia to said dinitrile is in the range of from about 2:1 to about 20:1.

7. The process according to claim 1 wherein said metal catalyst is supported on an inorganic support.

8. The process according to claim 7 wherein said inorganic support is magnesium oxide.

9. The process according to claim 1 wherein said metal catalyst is selected from the group consisting of iron, cobalt, nickel, and combinations of two or more thereof.

10. The process according to claim 6 wherein said metal catalyst is supported on magnesium oxide.

11. The process according to claim 10 wherein said metal catalyst is selected from the group consisting of iron, cobalt, nickel, and combinations of two or more thereof.

12. The process according to claim 1 wherein said additive is selected from the group consisting of organic amides, organic esters, carboxylic acids, salts of carboxylic acids, urea, and combinations of two or more thereof.

13. The process according to claim 12 wherein said additive is an amide.

14. The process according to claim 12 where said additive is a carboxylic acid salt.

15. The process according to claim 12 where said additive is an ester.

16. The process according to claim 12 wherein said additive is urea.

17. A process according to claim 1 wherein said additive is selected from the group consisting of formamide, acetamide, N-methyl formamide, N,N-dimethyl formamide, N-methylacetamide, N-methyldodecanamide, methyl formate, ethyl formate, sodium formate, ammonium formate, urea, and combinations of two or more thereof.

18. The process according to claim 17 wherein said metal catalyst is contacted with said additives to produce an additive-treated metal catalyst before being contacted with said dinitrile.

19. The process according to claim 18 wherein said dinitrile is selected from the group consisting of adiponitrile, ethylsuccinonitrile, methylglutaronitrile, alpha, omega-dodecanedinitrile, and combinations of two or more thereof.

20. The process according to claim 18 wherein said dinitrile is selected from the group consisting of adiponitrile, ethylsuccinonitrile, methylglutaronitrile, dodecanedinitrile, and combinations of two or more thereof.

21. A process comprising contacting a dinitrile with hydrogen in the presence of a solvent comprising liquid ammonia or an alcohol, a metal sponge catalyst comprising at least one metal selected from the group consisting of nickel, cobalt and iron, and an additive under a condition sufficient to effect the production of an aminonitrile wherein said dinitrile has about 4 to about 12 carbon atoms per molecule;

the molar ratio of said ammonia to said dinitrile is in the range of from about 2:1 to about 20:1; and said additive is selected from the group consisting of formamide, acetamide, N-methyl formamide, N,N-dimethyl formamide, N-methylacetamide, N-methyldodecanamide, methyl formate, ethyl formate, sodium formate, ammonium formate, urea, and combinations of two or more thereof.

22. The process according to claim 21 wherein said metal is contacted with said additive to produce an additive-treated metal catalyst before being contacted with said dinitrile.

23. A process for selectively hydrogenating adiponitrile to aminocapronitrile comprising contacting, at a temperature in the range of from about 60° C. to about 80° C. under a pressure in the range of from about 250 to about 2000 pounds per square inch, said adiponitrile with hydrogen in the presence of a solvent which comprises an alcohol or liquid ammonia, a metal sponge catalyst comprising iron and nickel, and an additive selected from the group consisting of formamide, acetamide, N-methyl formamide, N,N-dimethyl formamide, N-methylacetamide, N-methyldodecanamide, methyl formate, ethyl formate, sodium formate, ammonium formate, urea, and combinations of two or more thereof, wherein the nickel content in said catalyst is in the range of from about to 25 to about 35% based on the total weight of said catalyst and the molar ratio of said ammonia to said adiponitrile is in the range of from about 2:1 to about 20:1.

24. The process according to claim 23 wherein said metal is contacted with said additive to produce an additive-treated metal before being contacted with said dinitrile.

25. The process according to claim 24 further comprising recovering said aminocapronitrile.

* * * * *

UNITED STATES PATENT AND TRADEMARK OFFICE
CERTIFICATE OF CORRECTION

PATENT NO. : 5,986,127
DATED : November 16, 1999
INVENTOR(S) : Ionkin et al.

It is certified that error appears in the above-identified patent and that said Letters Patent is hereby corrected as shown below:

Column 1, line 10, delete [TE], add --THE--

Column 2, line 7, delete [methyleneoctanedkiitrile], add --methyleneoctanedinitrile--

Column 2, line 47, add --.-- after "thereof"

Column 2, line 61, add --.-- after "thereof"

Column 2, line 65, add --.-- after "thereof"

Column 3, line 15, add --.-- after "thereof"

Column 4, line 34, add --.-- after "catalyst"

Column 5, line 40, delete [Mi], add --Ni--

Column 5, line 50, add --.-- after "Formamide"

Column 6, line 15, delete [AWN], add --ADN--

Column 6, line 30, delete [aminocapronitrie], add --aminocapronitrile--

Column 7, line 14, delete [nm], add --mL--

Signed and Sealed this

Third Day of April, 2001

*Attest:*

NICHOLAS P. GODICI

*Attesting Officer*   *Acting Director of the United States Patent and Trademark Office*